United States Patent
Cannestra

(10) Patent No.: US 10,098,674 B2
(45) Date of Patent: Oct. 16, 2018

(54) SYSTEM AND METHOD FOR POSTERIOR CERVICAL FUSION

(71) Applicant: NuVasive, Inc., San Diego, CA (US)

(72) Inventor: Andrew F. Cannestra, Jacksonville, FL (US)

(73) Assignee: NuVasive, Inc., San Diego, CA (US)

( * ) Notice: Subject to any disclaimer, the term of this patent is extended or adjusted under 35 U.S.C. 154(b) by 38 days.

(21) Appl. No.: 14/623,988

(22) Filed: Feb. 17, 2015

(65) Prior Publication Data

US 2015/0230834 A1 Aug. 20, 2015

Related U.S. Application Data

(63) Continuation-in-part of application No. 13/503,050, filed as application No. PCT/US2010/053497 on Oct. 21, 2010, now Pat. No. 9,204,906.

(60) Provisional application No. 61/253,886, filed on Oct. 22, 2009, provisional application No. 61/940,186, filed on Feb. 14, 2014.

(51) Int. Cl.
*A61B 17/17* (2006.01)
*A61B 17/70* (2006.01)

(52) U.S. Cl.
CPC ...... *A61B 17/7064* (2013.01); *A61B 17/1757* (2013.01); *A61B 17/1703* (2013.01)

(58) Field of Classification Search
CPC .................................................. A61B 17/1671
USPC ..................................... 606/96–98, 104, 247
See application file for complete search history.

(56) References Cited

U.S. PATENT DOCUMENTS

| | | | |
|---|---|---|---|
| 4,907,577 A | 3/1990 | Wu |
| 5,099,494 A | 3/1992 | Kingston |
| 5,395,317 A | 3/1995 | Kambin |
| 5,431,658 A | 7/1995 | Moskovich |
| 5,464,864 A | 11/1995 | King |
| 5,531,751 A | 7/1996 | Schultheiss |
| 5,568,742 A | 10/1996 | Bauer |
| 5,571,109 A | 11/1996 | Bertagnoli |
| 5,586,840 A | 12/1996 | Nishio |
| 5,662,197 A | 9/1997 | Tabe |
| 5,669,915 A | 9/1997 | Caspar |
| 5,762,629 A | 6/1998 | Kambin |
| 5,837,209 A | 11/1998 | Saegusa |
| 6,063,088 A | 5/2000 | Winslow |
| 6,113,602 A | 9/2000 | Sand |
| 6,162,239 A | 12/2000 | Manhes |
| 6,228,022 B1 | 5/2001 | Friesem |
| 6,267,763 B1 | 7/2001 | Castro |
| 6,270,498 B1 | 8/2001 | Michelson |

(Continued)

FOREIGN PATENT DOCUMENTS

| | | |
|---|---|---|
| EP | 0077159 A1 | 4/1982 |
| EP | 1923007 A1 | 5/2008 |

(Continued)

*Primary Examiner* — Jan Christopher Merene

(57) ABSTRACT

This application describes surgical instruments and implants for building a posterior fixation construct across one or more segments of the cervical spinal column. The construct includes a sled adapted for positioning in a facet joint and two receivers slideably mounted on the sled. The receivers are adapted to support surgical instruments such as a drill, a tap, and a screw. The sled assists in orienting the instruments at a desired angle with respect to the spine.

20 Claims, 18 Drawing Sheets

(56) References Cited

U.S. PATENT DOCUMENTS

| | | |
|---|---|---|
| 6,428,541 B1 | 8/2002 | Boyd |
| 6,436,098 B1 | 8/2002 | Michelson |
| 6,440,139 B2 | 8/2002 | Michelson |
| 6,443,987 B1 | 9/2002 | Bryan |
| 6,447,512 B1 | 9/2002 | Landry |
| 6,508,827 B1 | 1/2003 | Manhes |
| 6,540,753 B2 | 4/2003 | Cohen |
| 6,575,981 B1 | 6/2003 | Boyd |
| 6,648,895 B2 | 11/2003 | Burkus |
| 6,656,205 B1 | 12/2003 | Manhes |
| 6,692,434 B2 | 2/2004 | Ritland |
| 6,725,080 B2 | 4/2004 | Melkent |
| 6,743,234 B2 | 6/2004 | Burkus |
| 6,929,647 B2 | 8/2005 | Cohen |
| 6,960,216 B2 | 11/2005 | Kolb |
| 6,969,392 B2 | 11/2005 | Gitis |
| 7,033,362 B2 | 4/2006 | McGahan |
| 7,074,226 B2 | 7/2006 | Roehm |
| 7,083,623 B2 | 8/2006 | Michelson |
| 7,118,576 B2 | 10/2006 | Gitis |
| 7,153,304 B2 | 12/2006 | Robie |
| 7,166,073 B2 | 1/2007 | Ritland |
| 7,226,452 B2 | 6/2007 | Zubok |
| 7,314,851 B2 | 1/2008 | Meesilpa |
| 7,338,527 B2 | 3/2008 | Blatt |
| 7,396,360 B2 | 7/2008 | Lieberman |
| 7,399,303 B2 | 7/2008 | Michelson |
| 7,431,722 B1 | 10/2008 | Michelson |
| 7,491,205 B1 | 2/2009 | Michelson |
| 7,507,242 B2 | 3/2009 | Triplett |
| 7,527,629 B2 | 5/2009 | Link |
| 7,569,054 B2 | 8/2009 | Michelson |
| 7,591,851 B2 | 9/2009 | Winslow |
| 7,615,079 B2 | 11/2009 | Flickinger |
| 7,635,370 B2 | 12/2009 | Michelson |
| 7,722,619 B2 | 5/2010 | Michelson |
| 7,731,721 B2 | 6/2010 | Rathbun |
| 7,740,635 B2 | 6/2010 | Lieberman |
| 7,776,046 B2 | 8/2010 | Boyd |
| 7,776,047 B2 | 8/2010 | Fanger |
| 7,780,675 B2 | 8/2010 | Schneid |
| 7,824,431 B2 | 11/2010 | McCormack |
| 7,837,713 B2 | 11/2010 | Petersen |
| 7,909,829 B2 | 3/2011 | Patel |
| 7,918,878 B2 | 4/2011 | Songer |
| 7,935,123 B2 | 5/2011 | Fanger |
| 7,959,677 B2 | 6/2011 | Landry |
| 8,016,831 B2 | 9/2011 | Gil |
| 8,025,678 B2 | 9/2011 | Reynolds |
| 8,075,591 B2 | 12/2011 | Ludwig |
| 8,105,362 B2 | 1/2012 | Duarte |
| 8,109,934 B2 | 2/2012 | Guenther |
| 8,123,786 B2 | 2/2012 | Lins |
| 8,142,440 B2 | 3/2012 | Dace |
| 8,152,714 B2 | 4/2012 | Garcia-Bengochea |
| 8,172,854 B2 | 5/2012 | Blain |
| 8,231,661 B2 | 7/2012 | Carls |
| 8,282,642 B2 | 10/2012 | McClintock |
| 8,298,235 B2 | 10/2012 | Grinberg |
| 8,323,292 B2 | 12/2012 | Dudasik |
| 8,328,814 B2 | 12/2012 | Klingseis |
| 8,328,815 B2 | 12/2012 | Farr |
| 8,337,500 B2 | 12/2012 | Bertagnoli |
| 8,366,748 B2 | 2/2013 | Kleiner |
| 8,394,107 B2 | 3/2013 | Fanger |
| 8,425,530 B2 | 4/2013 | Winslow |
| 8,465,495 B2 | 6/2013 | Belliard |
| 8,491,585 B2 | 7/2013 | Hannani |
| 8,523,865 B2 | 9/2013 | Reglos |
| 8,579,909 B2 | 11/2013 | Burkus |
| 8,641,719 B2 | 2/2014 | Gephart |
| 8,663,293 B2 | 3/2014 | Assell |
| 2002/0138079 A1 | 9/2002 | Cohen |
| 2002/0161366 A1 | 10/2002 | Robie |
| 2003/0195520 A1 | 10/2003 | Boyd |
| 2005/0159756 A1 | 7/2005 | Ray |
| 2005/0261770 A1 | 11/2005 | Kuiper |
| 2006/0149289 A1* | 7/2006 | Winslow ............ A61F 2/4405 606/102 |
| 2006/0220156 A1 | 10/2006 | Saito |
| 2006/0235391 A1 | 10/2006 | Sutterlin |
| 2006/0247633 A1 | 11/2006 | Winslow |
| 2007/0123905 A1 | 5/2007 | Schneid |
| 2007/0123985 A1* | 5/2007 | Errico ............ A61B 17/025 623/17.11 |
| 2007/0135814 A1 | 6/2007 | Farris |
| 2007/0233150 A1 | 10/2007 | Blain |
| 2008/0161810 A1 | 7/2008 | Melkent |
| 2008/0167655 A1 | 7/2008 | Wang |
| 2008/0234684 A1* | 9/2008 | Gil ............ A61B 17/1757 606/87 |
| 2009/0062857 A1 | 3/2009 | Ramsay |
| 2009/0062918 A1 | 3/2009 | Wang |
| 2009/0138091 A1 | 5/2009 | Ray |
| 2009/0177237 A1 | 7/2009 | Zucherman |
| 2009/0234397 A1 | 9/2009 | Petersen |
| 2010/0023013 A1 | 1/2010 | Flickinger |
| 2010/0121378 A1 | 5/2010 | Malek |
| 2010/0145391 A1 | 6/2010 | Kleiner |
| 2010/0262200 A1 | 10/2010 | Ray |
| 2010/0268228 A1 | 10/2010 | Petersen |
| 2010/0324560 A1 | 12/2010 | Suda |
| 2011/0054537 A1 | 3/2011 | Miller |
| 2011/0118593 A1 | 5/2011 | Melkent |
| 2011/0307061 A1 | 12/2011 | Assell |
| 2012/0022597 A1 | 1/2012 | Gephart |
| 2012/0083849 A1 | 4/2012 | Neubardt |
| 2012/0089191 A1 | 4/2012 | Altarac |
| 2012/0136392 A1 | 5/2012 | Keegan |
| 2012/0253316 A1 | 10/2012 | Oktavec |
| 2012/0253353 A1 | 10/2012 | McBride |
| 2012/0265250 A1 | 10/2012 | Ali |
| 2012/0271312 A1 | 10/2012 | Jansen |
| 2012/0271357 A1 | 10/2012 | Arthur |
| 2012/0277801 A1 | 11/2012 | Marik et al. |
| 2013/0012955 A1 | 1/2013 | Lin |
| 2013/0033220 A1 | 2/2013 | Ueda |
| 2013/0103036 A1 | 4/2013 | McGhie |
| 2013/0110183 A1 | 5/2013 | Duggal |
| 2013/0123848 A1 | 5/2013 | Duggal |
| 2013/0211462 A1 | 8/2013 | Walker |
| 2013/0310839 A1 | 11/2013 | McCormack |
| 2013/0310942 A1 | 11/2013 | Abdou |
| 2014/0025121 A1 | 1/2014 | Foley |
| 2014/0088707 A1* | 3/2014 | Donner ............ A61B 17/68 623/17.11 |

FOREIGN PATENT DOCUMENTS

| | | |
|---|---|---|
| WO | WO-1995022285 | 8/1995 |
| WO | WO-2003020137 | 3/2003 |
| WO | WO-2008085445 | 7/2008 |
| WO | WO-2012024162 | 2/2012 |
| WO | WO-2013058737 | 4/2013 |

* cited by examiner

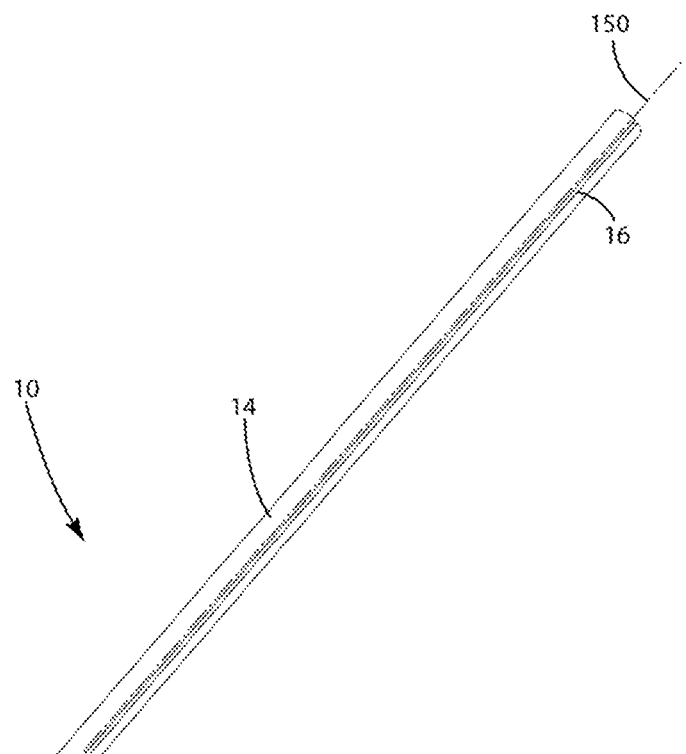
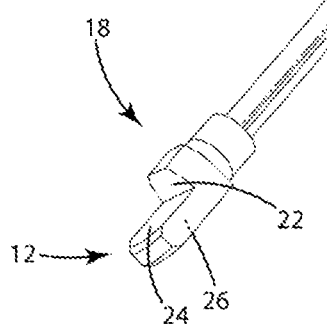
Fig. 2

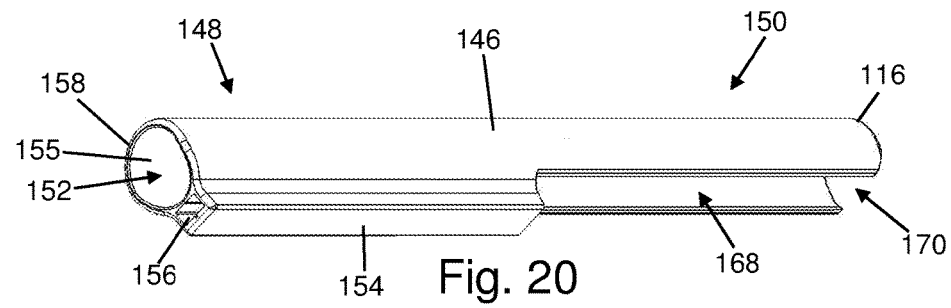
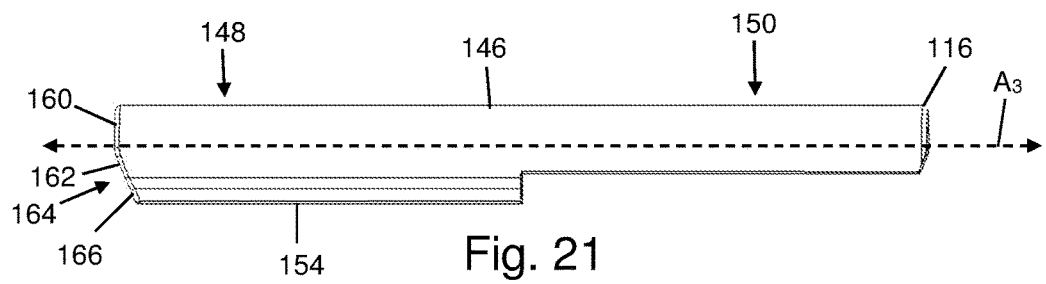
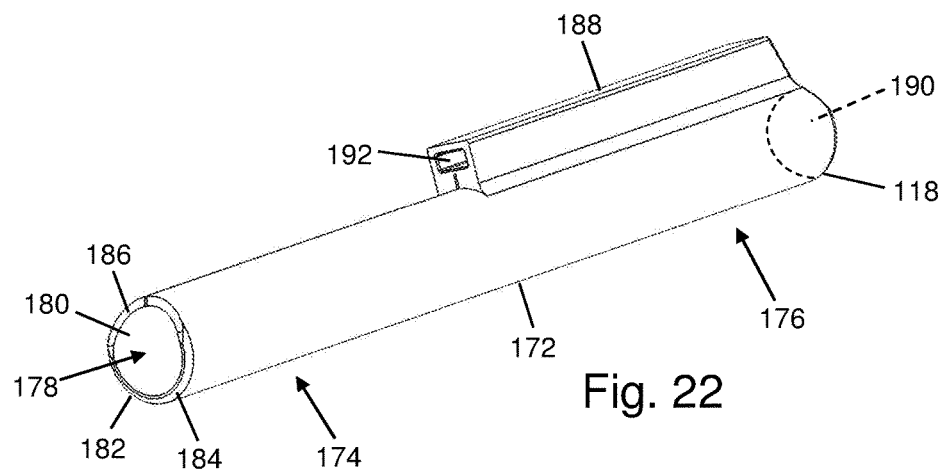
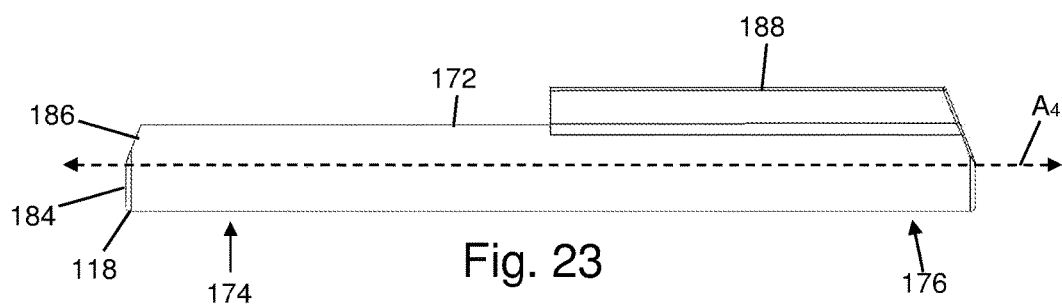

SYSTEM AND METHOD FOR POSTERIOR CERVICAL FUSION

CROSS-REFERENCES TO RELATED APPLICATIONS

This application is a non-provisional patent application claiming the benefit of priority under 35 U.S.C. 119(e) from U.S. Provisional Patent Application Ser. No. 61/940,186 filed on Feb. 14, 2014, and is a continuation-in-part of U.S. patent application Ser. No. 13/503,050, which is the National Stage of International Application No. PCT/US10/53497 filed Oct. 21, 2010, which claims the benefit of priority from U.S. Provisional Patent Application Ser. No. 61/253,886 filed on Oct. 22, 2009, the entire contents of which are hereby expressly incorporated by reference into this disclosure as if set forth in its entirety herein.

FIELD

This application describes surgical instruments and implants for building a posterior fixation construct across one or more segments of the cervical spinal column.

BACKGROUND

The facet joint or "zygapophysial" joint is a synovial joint between the superior articular process of one vertebra and the inferior articular process of the vertebra directly above it. There are two facet joints in each spinal motion segment (right and left). The biomechanical function of each pair of facet joints is to guide and limit movement of the spinal motion segment. These functions can be disrupted by degeneration, dislocation, fracture, injury, instability from trauma, osteoarthritis, and surgery.

Posterior cervical fusion surgery has become a common procedure for the treatment of degenerative disease of the cervical spine. In such surgery, fusion hardware, including plates and/or screws, are installed along the cervical spine to stabilize the bones, thereby facilitating fusion of the neck. Posterior cervical fusion has been shown to stabilize the cervical spine after decompression and eliminate the long-term risks of destabilization over time. However, current fusion hardware has considerable limitations due to the significant amount of soft tissue dissection required to place the hardware. While improved instruments and techniques have been developed for lumbar spine surgery, relatively fewer improvements have been developed in posterior cervical spine surgery.

Application of existing lumbar spine techniques to the cervical spine presents specific challenges that prohibit the simple modification of these techniques. For example, the anatomy of the cervical spine does not allow the safe placement of guide wires due to the vulnerability of the cervical spinal cord. Similarly, the presence of lateral masses and underlying vertebral arteries prohibit the use of cannulated hardware.

SUMMARY

The present invention overcomes the above noted problems, providing a unique method, hardware and technique to place posterior cervical spine screws.

According to one embodiment, a screw insertion technique includes inserting a screw system during open surgery or while using minimally invasive techniques. The screw insertion technique may also be used in a purely percutaneous fashion or through a tubular or expandable minimally invasive retractor system. The technique uses the facet joint to guide the screws into position. A spatula or "facet sled" is inserted within the facet joint under radiographic guidance. Once the sled is in place, the screws can be guided along the sled device enabling the placement of the screws based on the patient's natural anatomy. By placing the "sled" as a guide in the facet joint, the joint itself provides the trajectory for the screws to then be inserted. The screws will therefore have the appropriate cranial-caudal trajectory to improve accuracy for screw placement. The screws can be attached to towers similar to those used in lumbar systems to allow for insertion of the rod.

In another embodiment, the screw and tower design may be adapted to mate with the sled system for guidance into the facet joint.

The present invention has distinct advantages over prior art posterior screw systems. First, the invention provides a technique and assembly for placing screws in the posterior cervical spine. Second, the sled provides an accurate trajectory along the facet joint, which automatically provides the appropriate trajectory for each screw and reduces the likelihood of inaccurately placed screws in the superior/inferior trajectory.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 2 is a perspective view of a facet sled;

FIG. 20 is a perspective view a superior receptacle forming part of the posterior cervical fusion system of FIG. 15;

FIG. 21 is a plan view of the superior receptacle of FIG. 20;

FIG. 22 is a perspective view an inferior receptacle forming part of the posterior cervical fusion system of FIG. 15;

FIG. 23 is a plan view of the inferior receptacle of FIG. 22;

DETAILED DESCRIPTION OF A PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system and method for posterior cervical fusion disclosed herein boasts a variety of inventive features and components that warrant patent protection, both individually and in combination.

Figure 1:
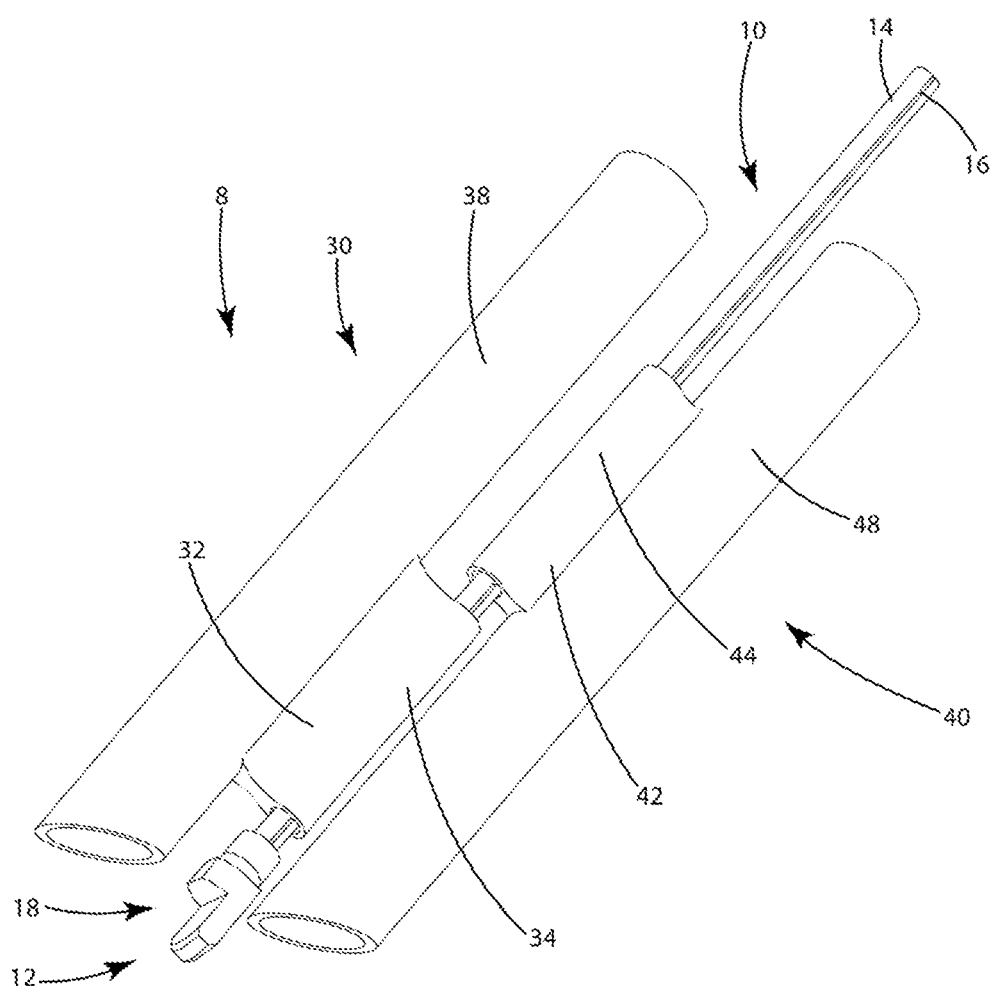
FIG. 1 is a perspective view of a posterior cervical screw insertion assembly in accordance with a first embodiment of the present invention.
Figure 6:
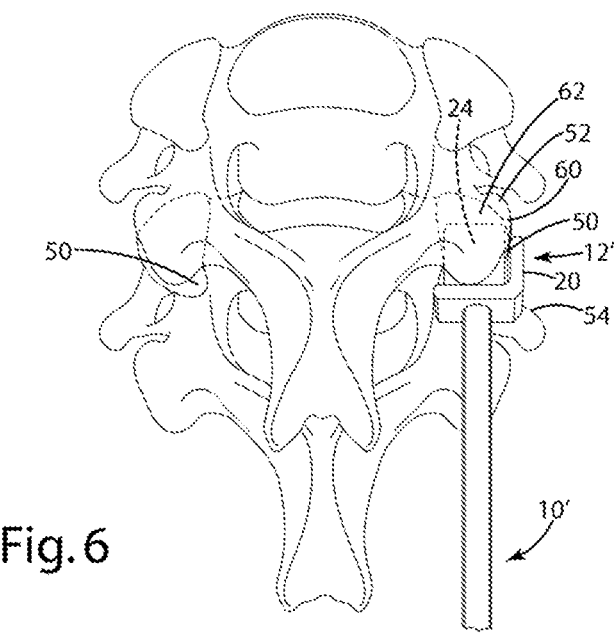
FIG. 6 is a posterior perspective view of a facet sled inserted into a facet joint.

An assembly for inserting posterior cervical screws is illustrated in FIG. 1 and is generally designated 8. The assembly 8 includes a facet sled or guide 10 having an end 12 that is adapted to be inserted within the facet joint 50 of a patient between a first vertebra 52 and a second vertebra 54. The end 12 may include a posterior guide or ridge 18 to limit the depth of insertion. As shown in FIG. 6, the facet sled 10' may also include lateral guides or ridges 20 to prevent medial migration during insertion. The facet sled 10 also includes an elongated handle 14 joined with and extending outward from the end 12.

Multiple embodiments are disclosed in this application. In the first embodiment, shown in FIG. 1, the assembly 8 includes a superior cylindrical extension 30, positioned substantially above the handle 14, and an inferior cylindrical extension 40, positioned substantially below the handle 14. As used in this context, the terms "above" and "below" are in reference to the handle 14 when the end 12 is inserted into the facet joint 50 between the first vertebra 52 and the second vertebra 54 and the patient is upright. In other words, "above" indicates a direction from the handle generally upward toward a patient's head, but away from the patient's body and "below" indicates a direction from the handle generally downward away from a patient's head but towards the patient's body.

As shown in FIG. 1, the superior cylindrical extension 30 and inferior cylindrical extension 40 are slidably coupled to the facet sled handle 14. The cylindrical extensions 30, 40 include elongated receptacles 38, 48, which are adapted to receive and guide the drill 200, tap and screws 70 with attached screw towers or extensions 72. Although the terms "cylindrical extension" and "elongated tube" may be used in this application, the extensions 30, 40 and tubes 38, 48 may be virtually any shape that will satisfy the functionality of the extension and tube.

Figure 3:
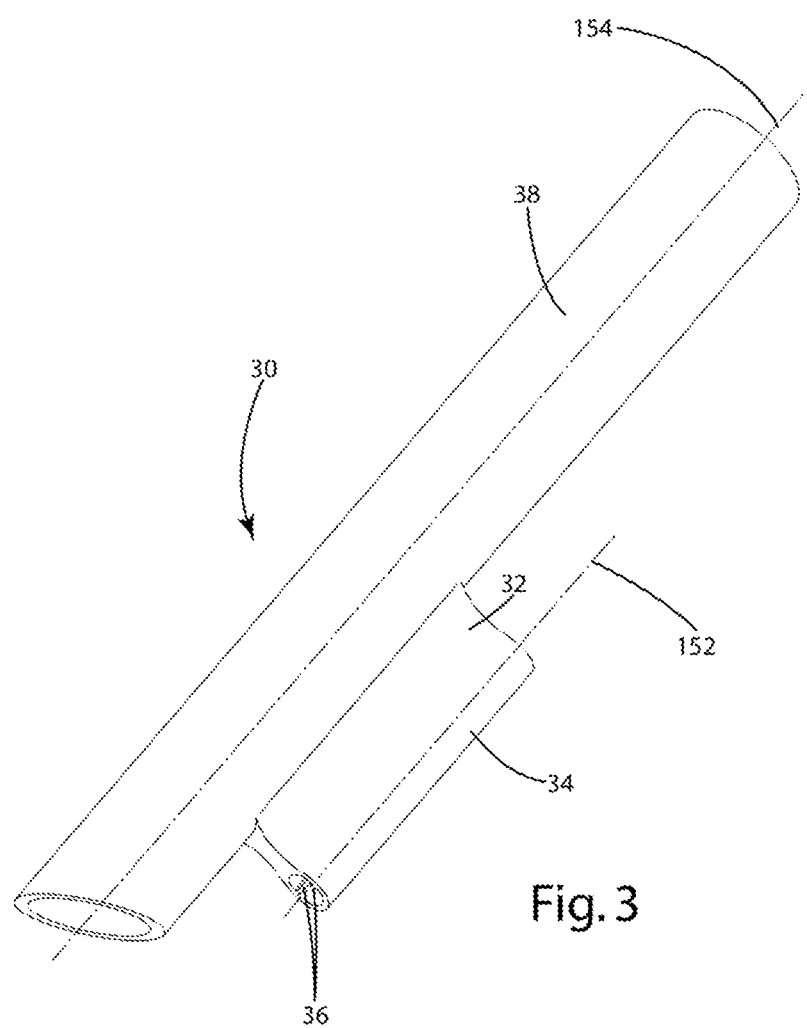
FIG. 3 is a perspective view of a superior cylindrical extension.
Figure 4:
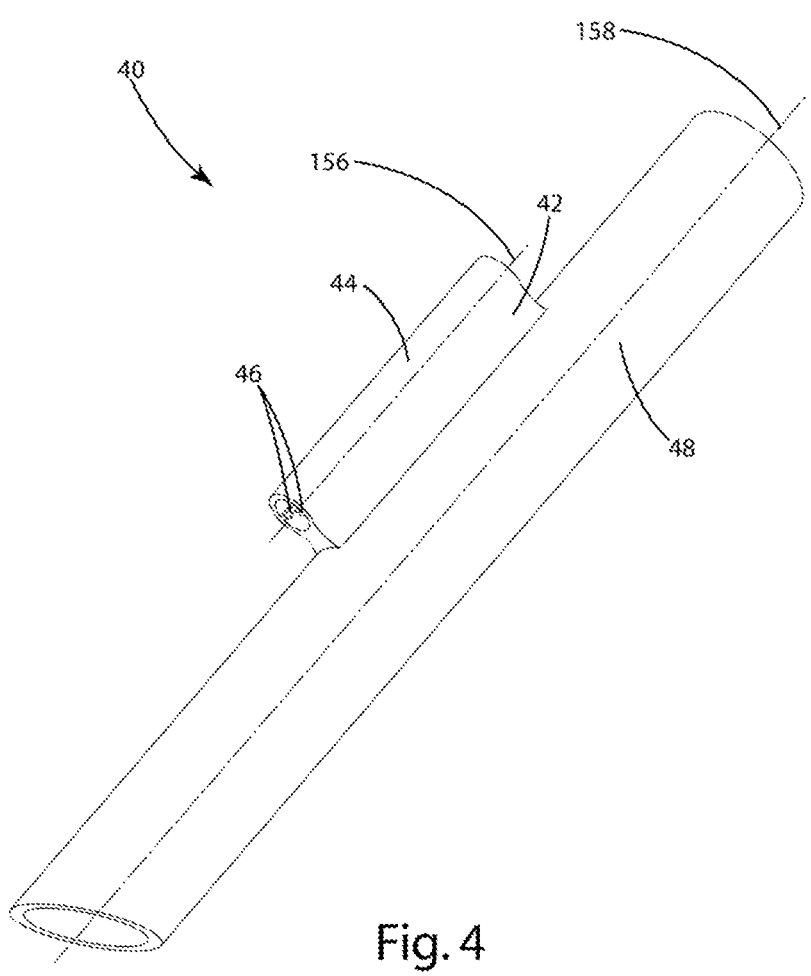
FIG. 4 is a perspective view of an inferior cylindrical extension.
Figure 5:
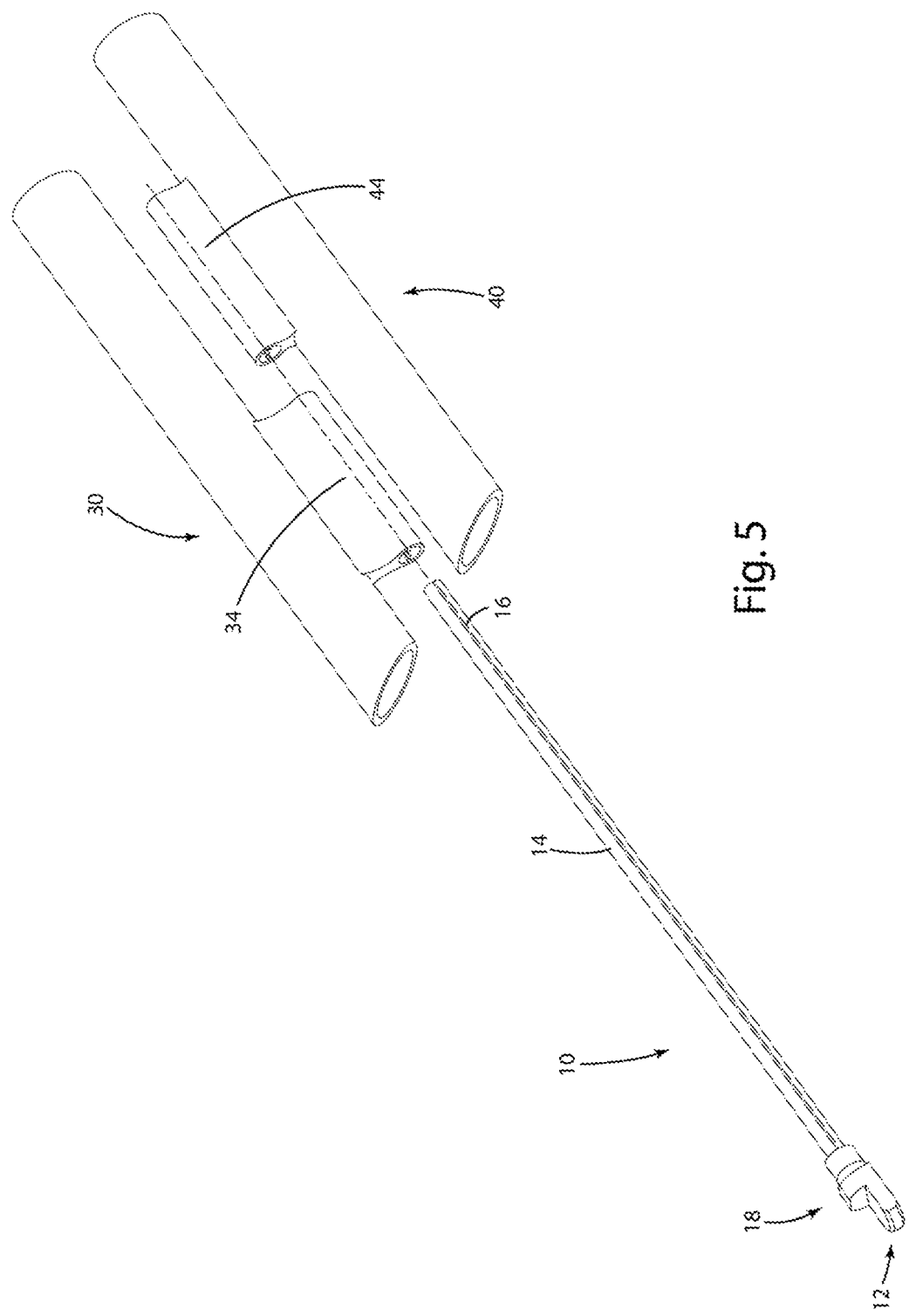
FIG. 5 is a perspective view of a superior cylindrical extension and an inferior cylindrical extension aligned with a handle of a facet sled.

As shown in FIGS. 3-5, the cylindrical extensions 30, 40 have offset guide members 32, 42, which mate with and travel down the facet handle 14. The offset of both the superior cylindrical extension 30 and the inferior cylindrical extension 40 from the handle 14 may be variable in size and/or angle to change the offset and angular position of the screw 70 relative to the facet sled 10. The insertion of the facet sled 10 into the facet joint 50 may allow the handle 14 of the facet sled 10 to establish the proper trajectory along which the screw towers 72 and other surgical instruments can travel to properly insert the screws 70 into the patient's spine 100.

Figure 13:
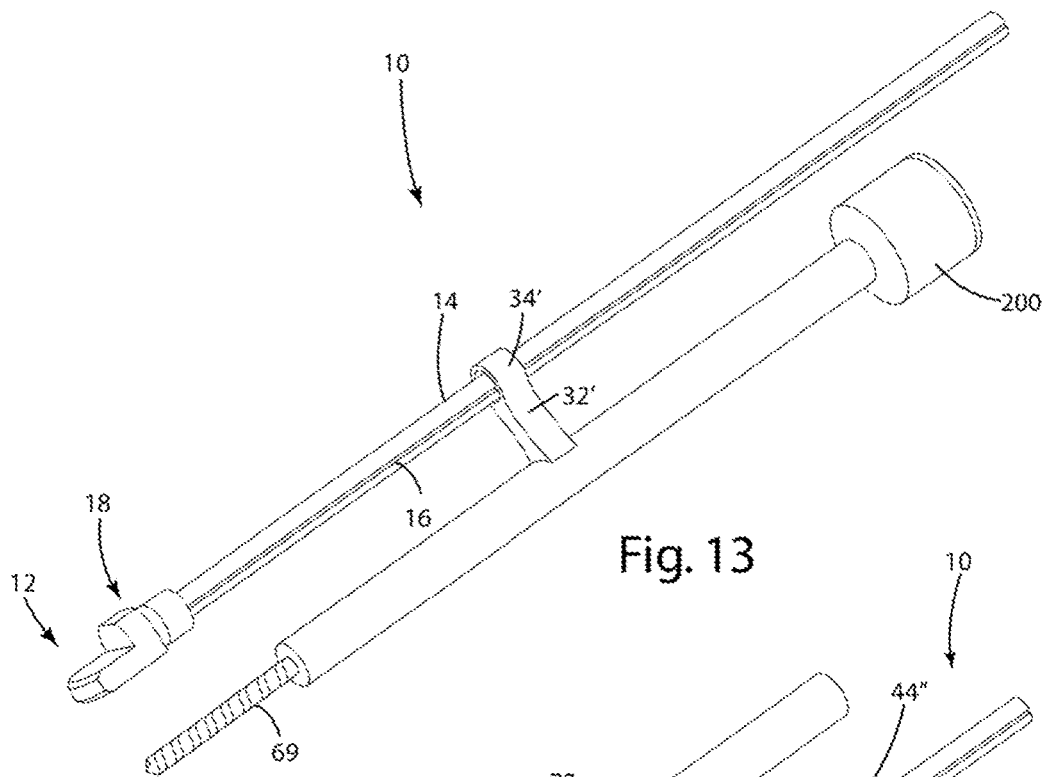
FIG. 13 is a perspective view of a facet sled and a drill in accordance with a second embodiment of the invention.
Figure 14:
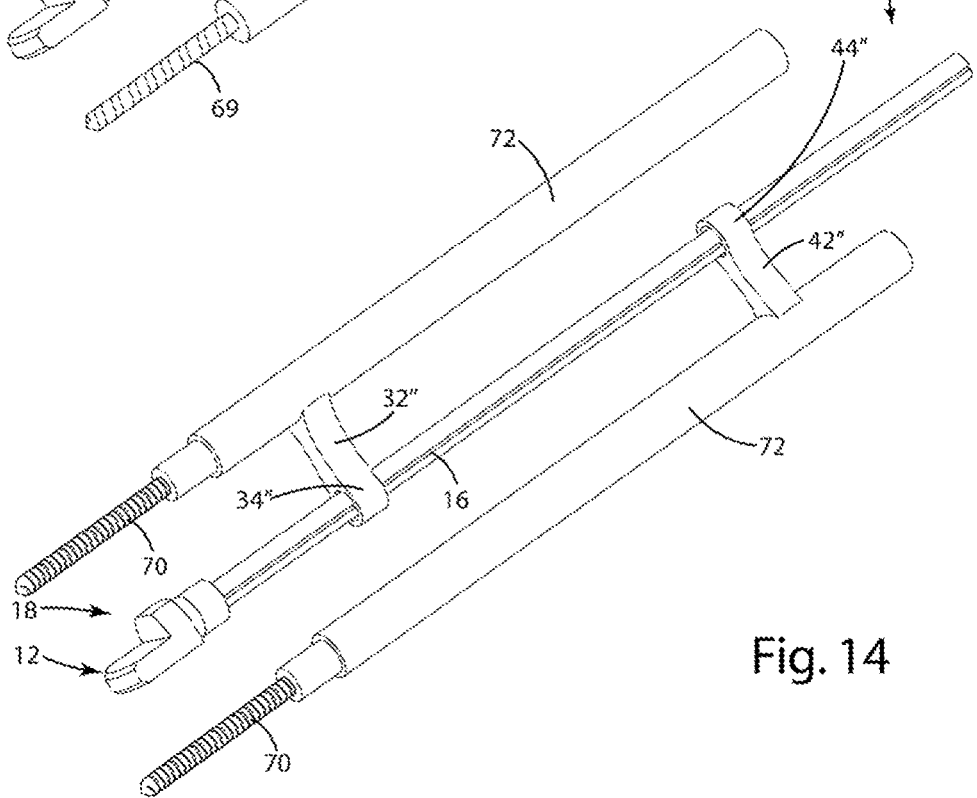
FIG. 14 is a perspective view of a facet sled and two screw towers in accordance with the second embodiment of the invention.

In the second embodiment, shown in FIGS. 13-14, the surgical instruments slidably engage the facet handle 14. In this embodiment, the assembly 8 may include at least one screw tower or extension 72, which is adapted to support a screw 70 for insertion into the patient's spine 100. Extending from the screw tower 72 is at least one guide member 32", 42", which engages and slides along the handle 14. The insertion of the facet sled 10 into the facet joint 50 allows the handle 14 of the facet sled to establish the proper trajectory along which the screw towers 72 and other surgical instruments can travel to properly insert the screws 70 into the patient's spine 100.

I. Structure

The facet sled 10 may be formed in any shape and size suitable to allow the sled 10 to be inserted into the facet joint 50 of the patient. As shown in FIG. 2, the end 12 of the facet sled is generally flat and is sized to slide between the vertebrae 52, 54 of the patient. The end 12 may optionally be tapered to further facilitate insertion between the vertebrae 52, 54. The end 12 includes a top surface 24, which is adapted to engage a top surface 56 of the facet joint 50, formed by vertebra 52, and a bottom surface 26, which is adapted to engage a bottom surface 58 of the facet joint 50, formed by vertebra 54 (see FIG. 7). At least a portion of the top surface of the sled 24 and/or bottom surface of the sled 26 may include rasping surfaces in order to decorticate the joint surface and promote arthrodesis.

A different configuration of the facet sled 10' and more specifically, a different configuration of the sled end 12', is shown in FIGS. 6-9. As shown in FIG. 6, a lateral guide 20 may be positioned along a side edge of the end 12' and may have a greater thickness and shorter length than the end 12', i.e. the lateral guide 20 may not extend as far outward from the handle 14 as does the end 12'. The lateral guide 20 may be adapted to engage a side surface 60 of the vertebra 52, as shown in FIG. 6. As a result of the lateral guide 20, there may be right and left sided facet sleds 10'. To improve versatility, the lateral guide 20 may be removable such that one end 12' may be capable of converting between a right and left sided facet sled 10'. The posterior guide 18 engages a front surface 62 of vertebra 52 with stop surface 22, which prevents the instrument from being inserted too deeply within the facet joint 50, as shown in FIG. 6. The sled end 12' may be movable medially and laterally (left and right in FIG. 6) to allow a user to position the handle at a desired medial/lateral angle about the patient's spine. The stop surface 22 may be positioned substantially perpendicularly to the lateral guide 20 to allow the user to select an appropriate medial/lateral angle, or the stop surface 22 may be positioned at various other angles with respect to lateral guide 20 such that the medial/lateral angle is predetermined when the sled end 12' is inserted into a facet joint 50. Optionally, the desired medial/lateral angle may be approximately 30°, which may create a diagonal trajectory into the vertebrae 52, 54. Further optionally, there may be rasping surfaces included on other surfaces of the sled 10. Further optionally, there may be a multitude of facet sleds 10 or removable ends 12 ranging in sizes to allow dilation of the facet joint 50 and rasping/cleaning of the surface prior to placement of the facet sled 10 or end 12 for screw insertion.

The handle 14 is elongated and is adapted to extend outward from a patient's spine 100 when the end 12 is inserted into the patient's facet joint 50. The handle 14 slidably receives, supports and guides the cylindrical extensions 30, 40 via placement of the handle receivers 34, 44 onto handle 14. The handle 14 defines at least one track 16 that is adapted to receive and guide the cylindrical extensions 30, 40. As shown in FIG. 2, the track 16 can be formed as a recess or notch in the surface of the handle 14 and can optionally extend lengthwise along the entire length of the handle 14. In this configuration, the cylindrical extensions 30, 40 may include handle receivers 34, 44 that include bosses or tongues 36, 46. The tongues 36, 46 may optionally extend lengthwise along the entire length of the inner surface of the handle receivers 34, 44 to match the track 16.

The tongues 36, 46 may be received within the track 16. More specifically, the tongues 36, 46 may be received by the same track 16 or separate tracks 16 on handle 14. Optionally, the track 16 may be positioned only in a selected location or in multiple locations along the handle 14. The track 16 and tongues 36, 46 cooperate to maintain the angular position of the handle receivers 34, 44, and therefore the angular position of the cylindrical extensions 30, 40, about a longitudinal axis 150 of the handle 14. Further optionally, different cylindrical extensions 30, 40 or different handle receivers 34, 44 may include tongues 36, 46 that position the cylindrical extensions 30, 40 at different angles about the longitudinal axis 150 of the handle 14 to accommodate different bone structures and patient needs. Further optionally, any suitable means for maintaining the angular position of the cylindrical extensions 30, 40 about the longitudinal axis 150 of the handle 14 may be used. As shown in FIG. 2, the handle 14 may extend in the same plane as the top surface 24 and bottom surface 26 of the end 12, so that the handle 14 can establish an accurate trajectory for the handle receivers 34, 44 and for the cylindrical extensions 30, 40. The facet sled 10, which may include the end 12, the posterior guide 18, the handle 14 and the lateral guide 20 can be integrally fabricated in a single piece, or could alternatively be fabricated from multiple pieces.

The cylindrical extensions 30, 40 can be formed in any suitable shape to support and guide the surgical instruments. As shown in FIGS. 3-4, the cylindrical extensions 30, 40 may include elongated receptacles 38, 48 to support and guide the surgical instruments. The elongated receptacles 38, 48 each have a longitudinal axis 154, 158, which may generally be referred to as the longitudinal axes of the cylindrical extensions 30, 40. In the embodiment of FIGS. 3-4, the elongated receptacles are shown as elongated tubes 38, 48. The elongated tubes 38, 48 may be attached to the handle receivers 34, 44 with guide members 32, 42.

The guide members 32, 42 may be joined with the elongated tubes 38, 48 and the handle receivers 34, 44 in any suitable manner. For example, the guide members 32, 42 may be integrally formed, welded, adhered or releasably attached to the elongated tubes 38, 48 and the handle receivers 34, 44. Various sizes of interchangeable guide members 32, 42 or various cylindrical extensions 30, 40 with various sizes of permanently placed guide members 32, 42 may provide various distances between the facet joint 50 and the screw placement. Further optionally, various guide members 32, 42 may place the elongated tubes 38, 48 at various angles with respect to the handle, such that the cylindrical extension 30, 40 or the guide member 32, 42 may be additionally selected based on a desired angle. The guide members 32, 42 may be of any configuration that will adequately support the elongated tubes 38, 48 with respect to the handle receivers 34, 44. For example, the guide members 32, 42 may be formed as tubular members extending generally perpendicularly from the elongated tubes 38, 48. Optionally, the guide members 32, 42 may also be a single narrow connecting member as shown in FIGS. 3-4. Further optionally, the guide members 32, 42 may be more than one narrow connecting member. The use of the handle receivers 34, 44 and guide members 32, 42 may assist in keeping the elongated tubes 38, 48 parallel to the handle 14 when the end 12 is within the facet joint 50, which is generally considered a proper trajectory for the drill 200, tap and screws 70 during a posterior cervical fusion surgery.

Figure 9:
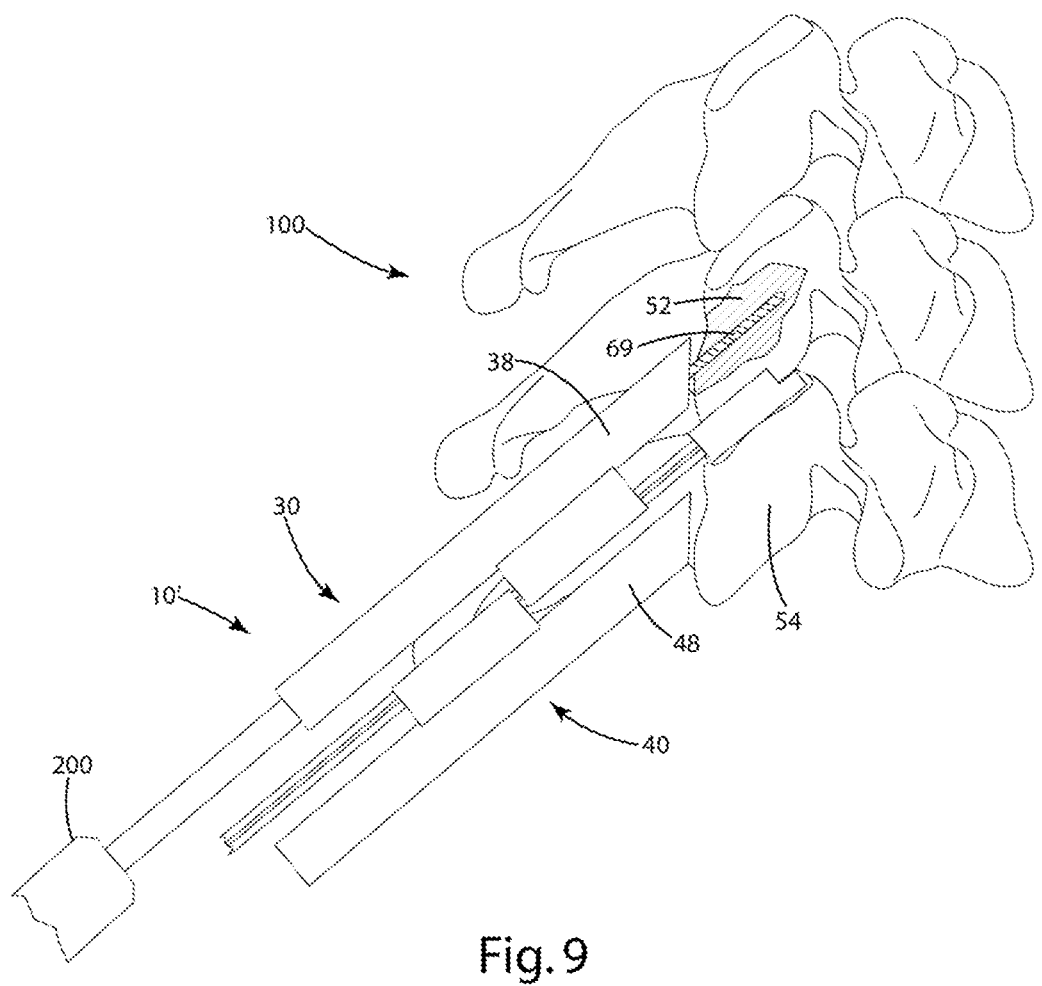
FIG. 9 is a side view of a facet sled inserted into a facet joint with a superior and an inferior cylindrical extension in place and a drill placed in the superior extension.
Figure 10:
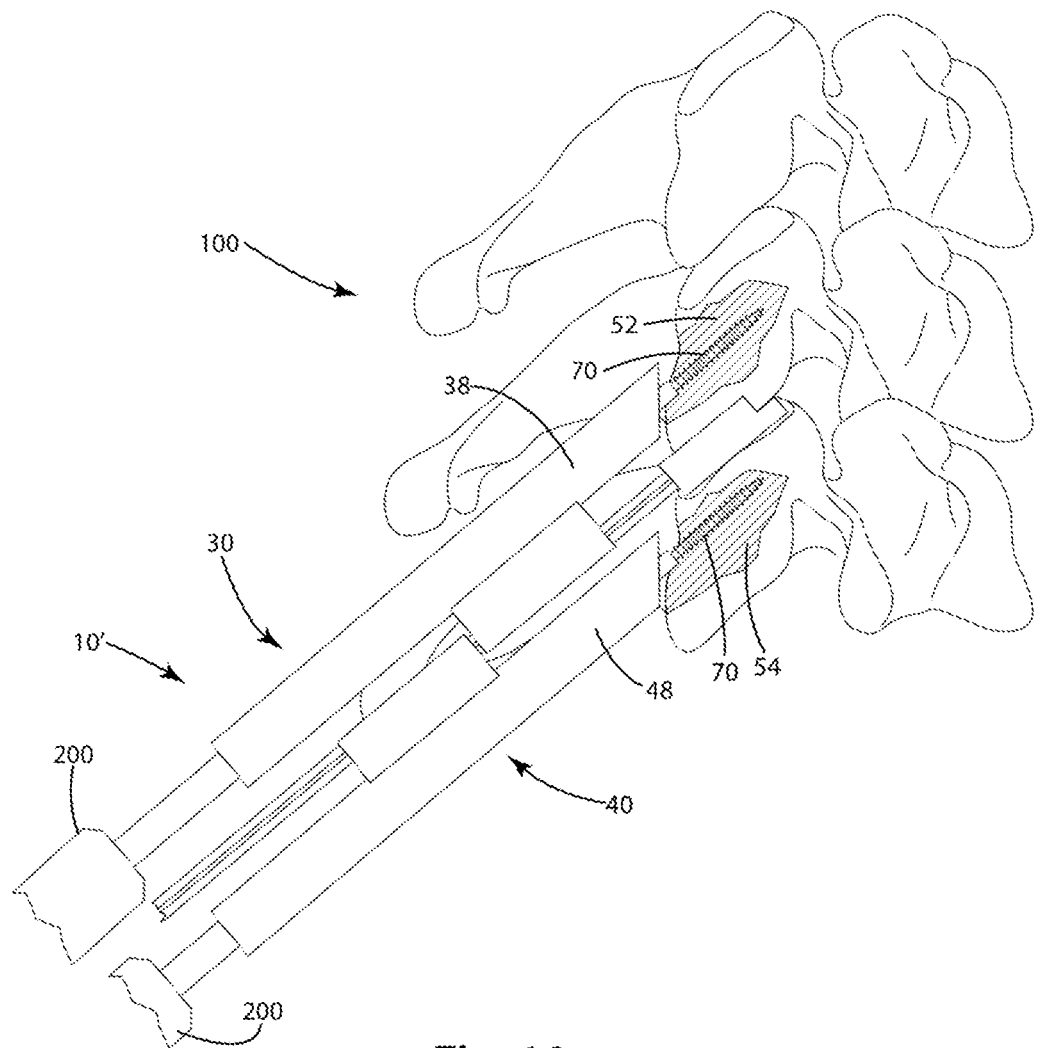
FIG. 10 is a side view of a facet sled inserted into a facet joint with a superior and an inferior cylindrical extension in place and screws placed through the extensions and into the vertebrae.
Figure 11:
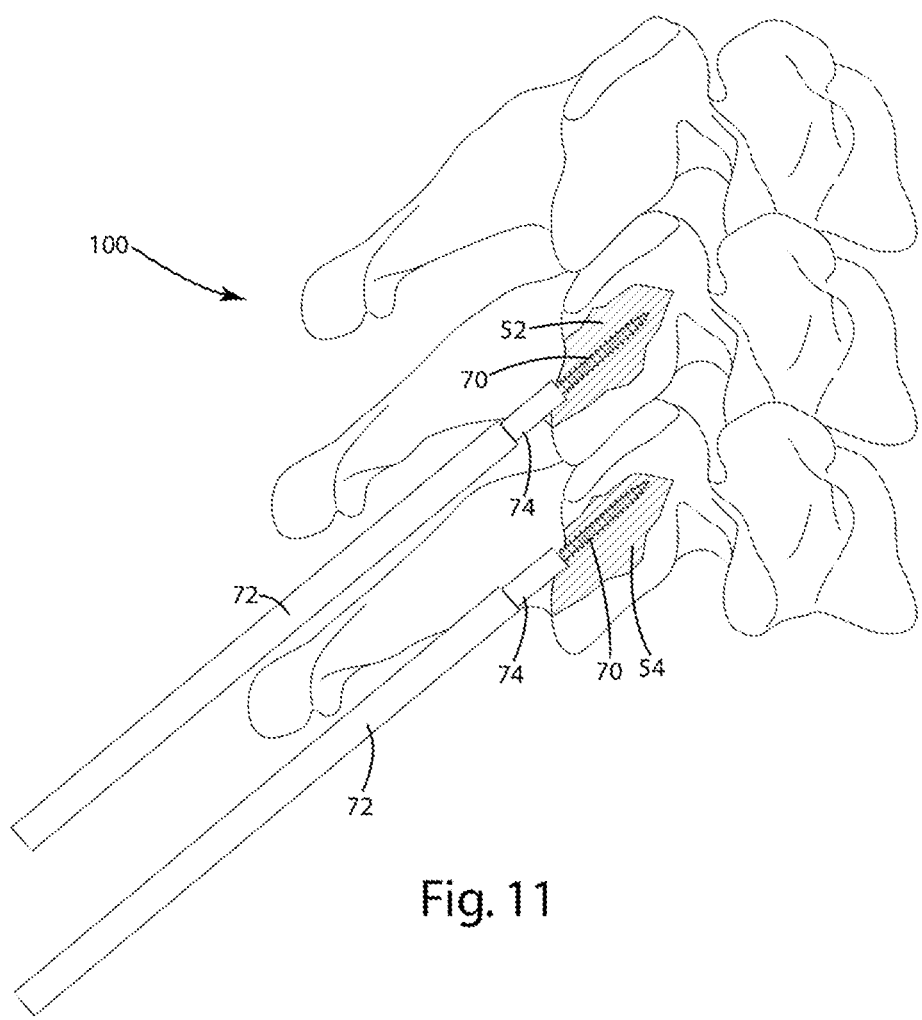
FIG. 11 is a side view of two screws in place with two attached screw towers.
Figure 12:
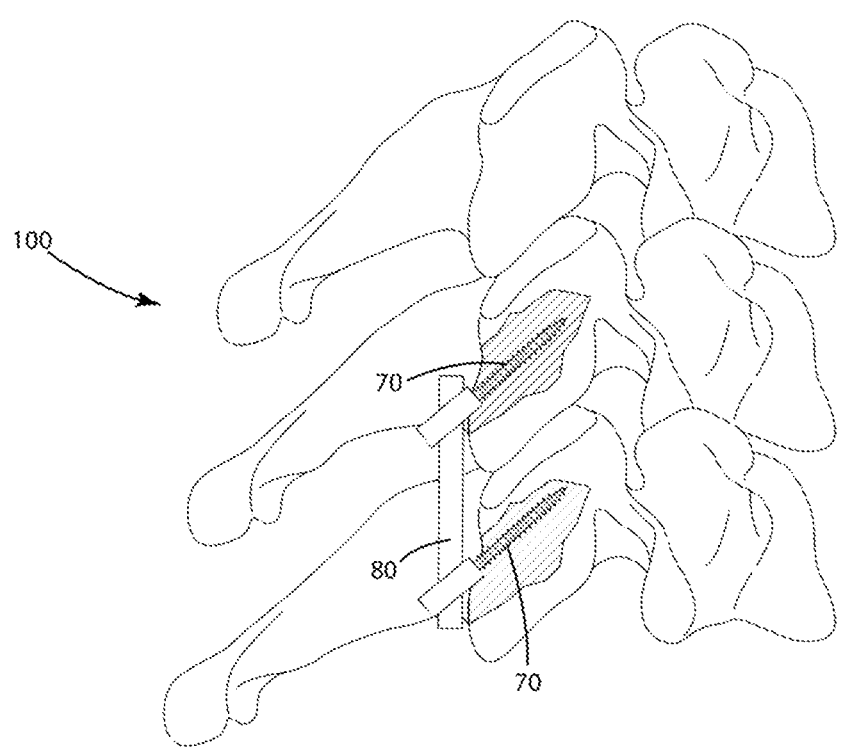
FIG. 12 is a side view of two screws in place with a rod for connecting the screws.

The screw towers 72 may retain the screws 70 in any suitable manner. For example, the front ends of the towers 72 may include a recess 74 adapted to receive and retain the screws 70 so that the screws 70 extend outward from the towers 72 in a lengthwise direction, as shown in FIGS. 11 and 14. In this configuration, the screws 70 are aligned with the screw towers 72 and are ready to be inserted into the patient's spine 100. The screw towers 72 may optionally be otherwise similar to towers used in lumbar spine surgery. As shown in FIGS. 9-11, the drill 200, threaded taps and screws 70 with attached towers 72 may be inserted through the elongated tubes 38, 48 to align these surgical instruments with the elongated tubes 38, 48 and to position the surgical instruments at the proper trajectory. As shown in FIG. 12, a connector rod 80 may be positioned between the screws 70 to complete the surgery.

In a second embodiment of the invention, shown in FIGS. 13 and 14, the surgical instruments may slidably engage the handle 14 such that the cylindrical extensions 30, 40 may be eliminated from the assembly. In this configuration, each of the instruments instead has its own removable handle receiver 34', 34", 44" to guide the instrument at the proper trajectory. In this embodiment, the instruments may include attachment points, recesses or protrusions at which the guide members 32', 32", 42" may be attached to the instruments. The length and angular orientation of the guide members 32', 32", 42" may vary depending on the distance and angle desired between the handle 14 and the instruments.

Suitable materials for the assembly 8 will be known to those skilled in the art and include metal, such as stainless steel and titanium, and plastics.

II. Installation and Use

Figure 7:
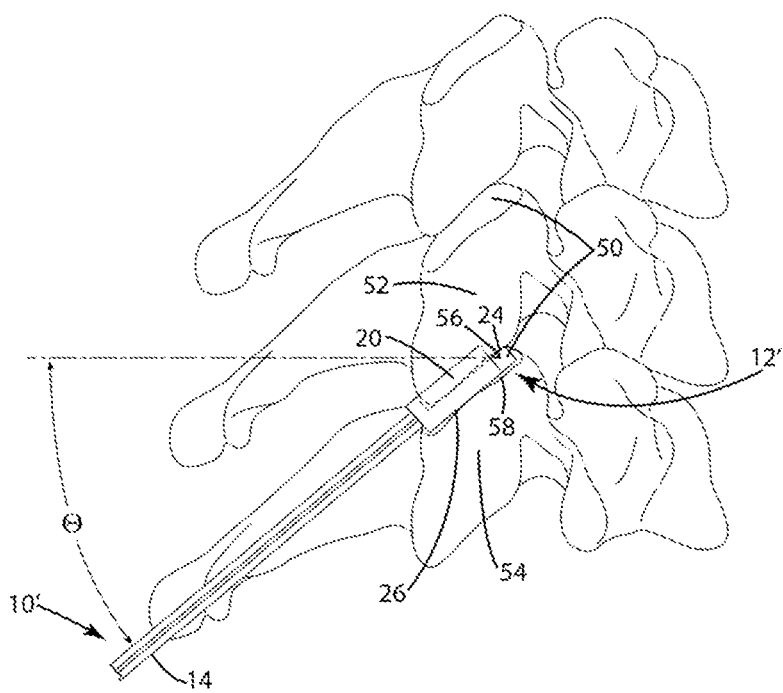
FIG. 7 is a side view of a facet sled inserted into a facet joint.
Figure 8:
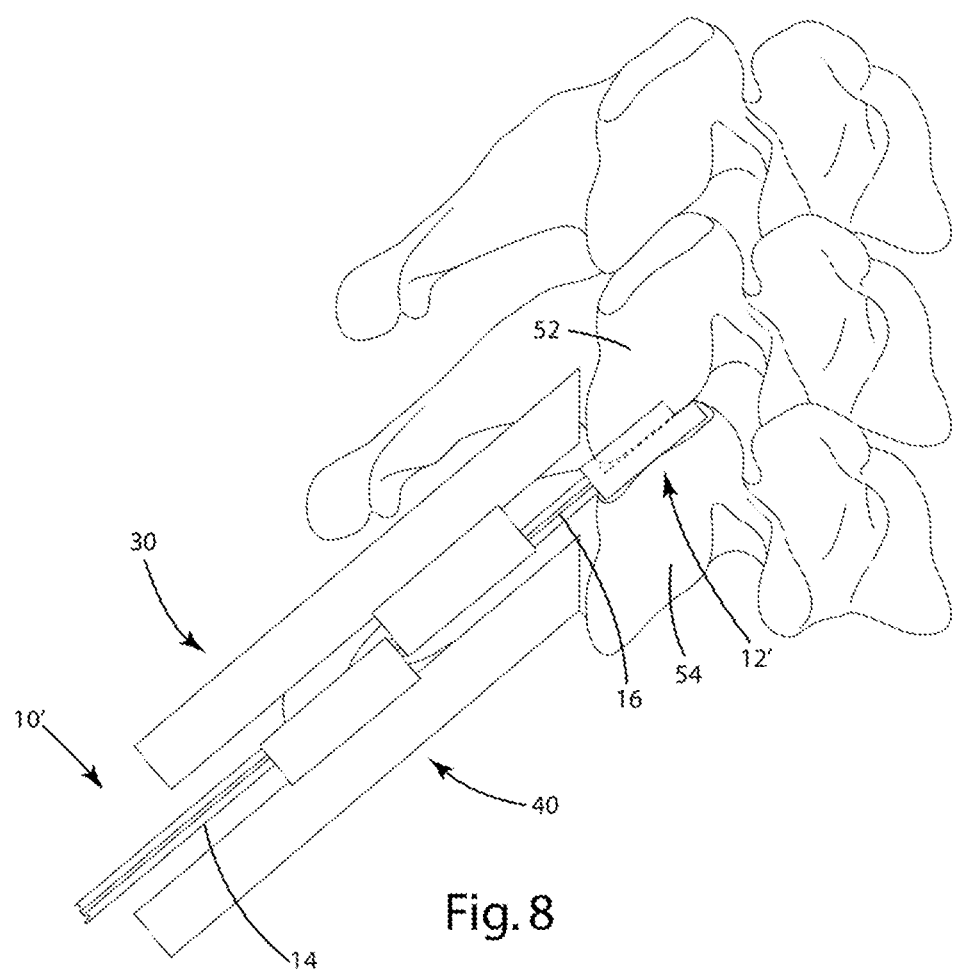
FIG. 8 is a side view of a facet sled inserted into a facet joint with a superior and an inferior cylindrical extension in place.

As shown in FIGS. 6-7, the facet sled end 12' is inserted within the facet joint 50 of the cervical spine 100, optionally using fluoroscopic guidance. The end 12' may be placed during open surgery or using minimally invasive techniques. The facet sled end 12' may also be placed in a purely percutaneous fashion or through a tubular or expandable minimally invasive retractor. As shown in FIG. 7, the sled end top surface 24 may engage the top surface 56 of the facet joint 50 and the sled end bottom surface 26 may engage the bottom surface 58 of the facet joint 50. As shown in FIG. 6, the lateral guide 20 may also engage a side surface 60 of the vertebra 52 and stop surface 22 may engage a front surface 62 of vertebra 52.

As shown in FIG. 7, the sled end 12', including top surface 24, bottom surface 26, lateral guide 20 and stop surface 22 may be sized and shaped so that placement of the end 12' in the facet joint 50 causes the handle 14 to extend outward from the spine at an angle θ, defining a trajectory into the facet complex. In the illustrated embodiment, the angle θ is a downward angle. Optionally, the angle θ may be a proper, preferred or optimum angle for screw insertion during a posterior cervical fusion surgery. Further optionally, the angle θ may be another angle based on the particular patient's bone structure. The sled end 12' may also allow for movement of the handle 14 medially or laterally (to the right and left in FIG. 6), which may allow a user to position the handle 14 at a desired medial/lateral angle about the patient's spine. Optionally, the stop surface 22 may be positioned at a predetermined angle with regard to the lateral guide 20, which may create a desired medial/lateral angle when the sled end 12' is inserted into a facet joint 50. Further optionally, the desired medial/lateral angle may be approximately 30°, which may create a diagonal trajectory for insertion of the screws 70. Inserting the screws 70 at a diagonal across the vertebrae 52, 54 may allow the user to insert longer screws 70 and therefore increase the strength of the fusion.

Once the facet sled 10, 10' is in place, the desired distance between the handle 14 and the screw placement is determined. Optionally, the desired angle between the elongated tubes 38, 48 and the handle 14 is also determined. An appropriate cylindrical extension 30, 40 (if the guide members 32, 42 are not removable) or an appropriate guide member 32, 42 (if the guide members 32, 42 are removable) may be selected based on the desired distance, desired angle between tubes 38, 48 and handle 14, and desired angle of tubes 38, 48 about the longitudinal axis 150 of the handle 14. The longitudinal axes 152, 156 of the handle receivers 34, 44 are aligned with the handle 14, shown in FIG. 5, and inserted onto the handle 14, shown in FIGS. 1 and 8. The bosses or tongues 36, 46 within the handle receivers 34, 44 may engage at least one track 16 defined in the handle 14 to maintain the handle receivers 34, 44 and elongated tubes 38, 48 at a desired angular position about the longitudinal axis 150 of the handle 14.

As shown in FIGS. 9-10, a number of instruments, including drills 200, threaded taps and screws 70 are inserted into the elongated tubes 38, 48 and are used to prepare the facet joint 50 and cervical spine 100 of the patient for placement of the screws 70. These instruments are inserted into the elongated tubes 38, 48 such that the instruments are positioned at the same angle as the elongated tubes 38, 48 with regard to the patient's spine 100.

As noted, optionally, the desired angle for the tubes 38, 48 and the instruments may be substantially parallel to the handle 14 such that the angle of the instruments is the angle θ, which is generally the proper trajectory along which the screw 70 should enter the spine 100. A drill 200 with drill bit 69 is shown in FIG. 9 inserted into the elongated tube 38 and forming a hole in vertebra 52. After the hole is formed, a threaded tap is inserted into the hole to provide threads that may engage a screw 70. Use of these instruments is known in the art and is typical during screw insertion procedures. Optionally, as shown in FIGS. 13 and 14, if a device in accordance with a second embodiment of the invention is used, the preparatory instruments may include attachment points and a user may select the appropriate guide members 32', 32", 42" such that the instruments may slide along the track 16 of the handle 14 at the desired distance, angle with respect to the handle 14 and angle about the longitudinal axis 150 of the handle 14.

To prepare the screw tower 72, the screw 70 is inserted into the end portion 74 of the screw tower 72 and the screw tower 72 is inserted into the elongated tubes 38, 48. Optionally, if a device in accordance with a second embodiment of the invention is used, one or more guide members 32", 42" may be joined with or otherwise attached to the screw tower 72 and the handle receiver 34", 44", as shown in FIG. 14. In this configuration, the screw tower 72 may slide along handle 14. As described in connection with the first embodiment above, the guide members 32", 42" may be of various configurations to provide users with various options for screw placement.

Once the facet joint 50 has been prepared for screw placement, the cylindrical extensions 30, 40 can then be selectively moved frontward and backward along the length of the handle 14. Optionally, in a second embodiment, the screw towers 72 may be moved along the length of handle 14. For example, a user could move the cylindrical extensions 30, 40 or the screw towers 72 toward the patient's spine 100 until the screw 70 engages the spine 100 and is threaded into the bone. The cylindrical extensions 30, 40 are shown in this position in FIG. 10. This process can be repeated for each screw 70, drill 200 and threaded tap that is inserted into the spine 100.

Once the screws 70 are in place, the facet sled 10, 10' and the cylindrical extensions 30, 40 may then be removed, as shown in FIG. 11. As shown in FIG. 11, the screw towers 72 may be left in place to allow manipulation of the screw heads at the level of the skin, to assist in subsequent connection of the screws 70 with a connector rod 80 and to assist with final completion of stabilization, as shown in FIG. 12. Optionally, a placement tool may be used to insert the connector rod 80 in either embodiment.

Figure 15:
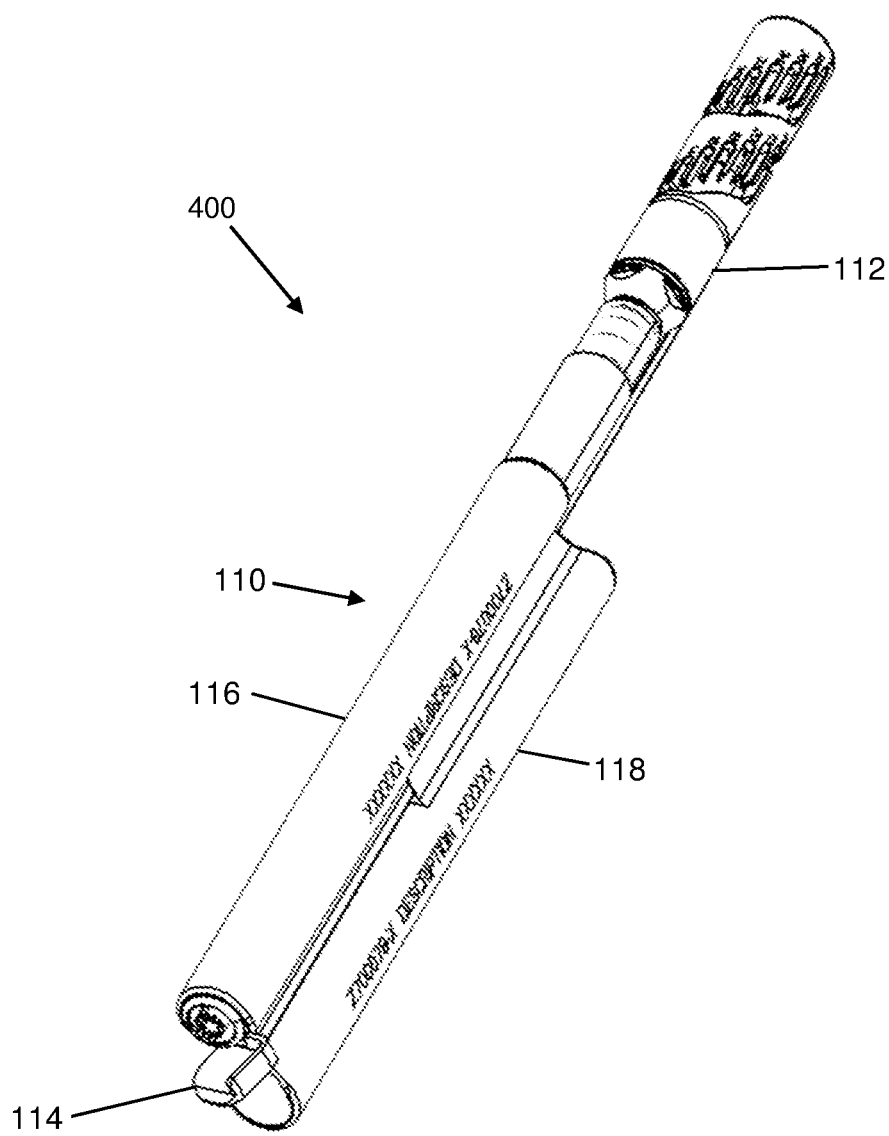
FIG. 15 is a perspective view of an example of a posterior cervical fusion system in accordance with an alternative embodiment, including a guide assembly and drill guide.
Figure 16:
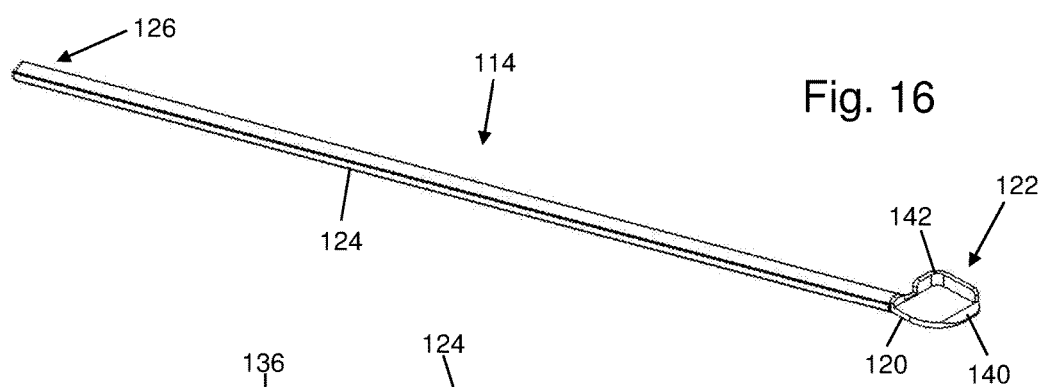
FIG. 16 is a perspective view of an example of a guide member forming part of the posterior cervical fusion system of FIG. 15.
Figure 17:
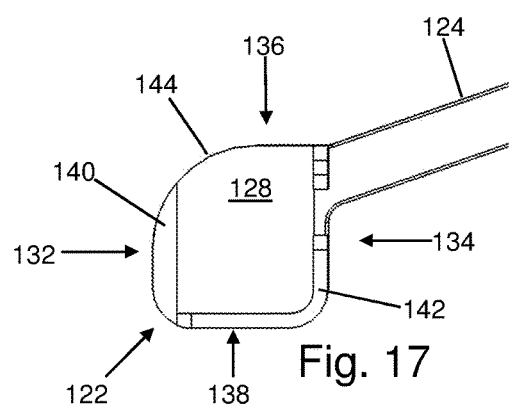
FIG. 17 is a top plan view of the distal end region of the guide member of FIG. 16.
Figure 18:
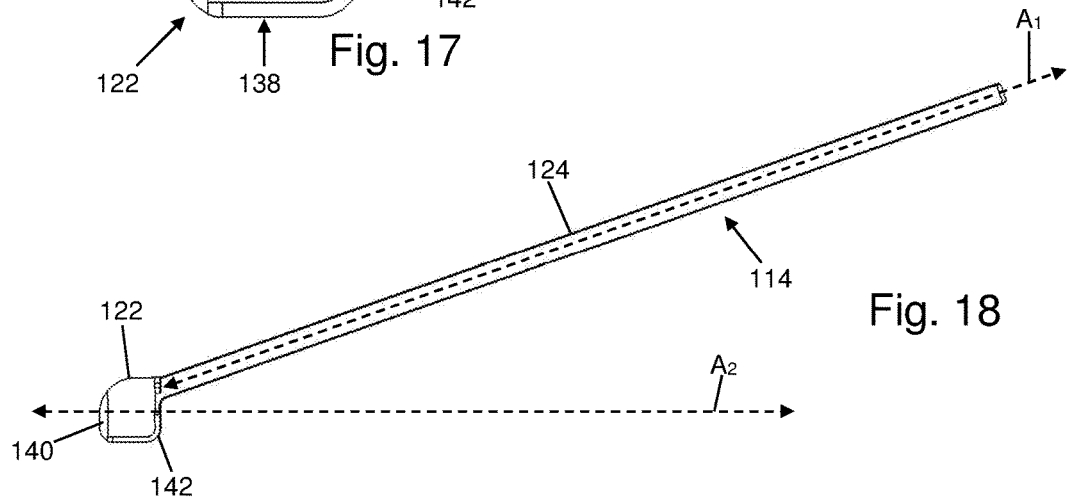
FIG. 18 is a top plan view of the guide member of FIG. 16.
Figure 19:
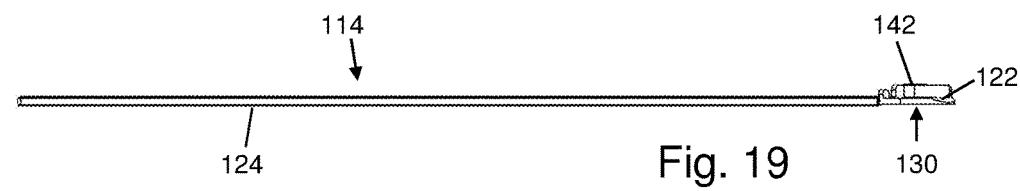
FIG. 19 is a plan view of the guide member of FIG. 16.

FIG. 15 illustrates an alternative exemplary embodiment of a posterior cervical fusion system, generally designated 400. The posterior cervical fusion system 400 of the instant embodiment includes a guide assembly 110 and a drill guide 112. The guide assembly 110 includes a guide member 114, a superior receptacle 116, an inferior receptacle 118, and an adjustable drill guide 116. As will be explained in further detail below, the guide member 114 of the current embodiment includes a stem having a non-circular cross-section extending proximally from a facet anchor 120 at the distal end. The facet anchor 120 is dimensioned for insertion into the facet joint to provide an anchor for the guide assembly 110 and to ensure proper angular positioning of the guide assembly (via the stem), which in turn ensures that the drill guide 112 is positioned properly prior to insertion of bone screws. The superior and inferior receptacles 116, 118 are each open at both the proximal and distal ends and are hollow throughout the length of the receptacle from the open proximal end to the open distal end. The superior and inferior receptacles 116, 118 are dimensioned to receive and support surgical instruments used in a posterior fusion procedure, for example including but not limited to the adjustable drill guide 112 of the present embodiment.

FIGS. 16-19 illustrate the guide member 114 in further detail. The guide member 114 comprises a facet anchor 120 at the distal 122 and a rigid elongated stem 124 extending away from the facet anchor 120 to the proximal end 126. The facet anchor 120 is similar to the facet sled 10 described above, and may be formed in any shape and size suitable to allow the anchor 120 to be inserted into the facet joint of the patient. By way of example, the facet anchor 120 is generally planar however other configurations are possible. The facet anchor 120 has a top surface 128, a bottom surface 130, a leading end 132, a trailing end 134, a medial side 136, and a lateral side 138. The top surface 128 is generally flat and is configured to engage the bony structure of a first vertebra forming part of the facet joint. The bottom surface 130 is also generally flat and is configured to engage the bony structure of the second, adjacent vertebra forming part of the facet joint. The leading end 132 includes a lead-in tapered surface 140 to facilitate distraction of the facet joint and insertion of the facet anchor 120 into the joint. Although not shown, at least one of the top and bottom surfaces 128, 130 may include a keel, serrations, or other anti-migration features to help stabilize the position of the facet anchor 120 within the facet joint. The facet anchor 120 further includes a raised wall 142 positioned on the top surface 128 along at least a portion of the trailing end 134 and lateral side 138. The raised wall 142 acts as a depth stop for the facet anchor 120 to prevent over-insertion into the facet joint. For example, the portion the raised wall 142 that is positioned along the trailing end 134 prevents the facet anchor 120 from advancing too far forward into the facet joint and the portion of the raised wall 142 positioned along the lateral side 138 prevents the facet anchor 120 from advancing too far medially. The antero-medial corner 144 of the anchor has a larger radius of curvature than the other corners to avoid violating nerve roots exiting adjacent the facet.

The stem 124 of the present example has a non-circular perimeter that acts to prevent the superior and inferior receptacles 116, 118 from rotating about the longitudinal axis $A_1$ of the stem 124 thereby stabilizing the positioning of the cervical fusion system 400. The stem 124 of the present example is shown by way of example only has having a generally rectangular perimeter, however a stem 124 having a perimeter comprising any other non-circular geometric shape is within the scope of this disclosure. The longitudinal axis $A_1$ of the stem 124 is medially offset from the axis of insertion $A_2$ of the facet anchor 120. The offset axis $A_1$ of the stem 124 allows for placement of screws having a medial to lateral trajectory through the lateral mass of a vertebra.

FIGS. 20 and 21 illustrate the superior receptacle 116 in more detail. The superior receptacle 116 comprises a generally cylindrical body 146 having a distal portion 148, a proximal portion 150, and a lumen 152 extending longitudinally through the body 146. The distal portion 148 includes a first extension 154 and a distal opening 155 (which constitutes the distal terminus of the lumen 152). The first extension 154 is positioned along the inferior aspect of the body 146, has a height dimension that is perpendicular the body 146 and a length dimension that is parallel to the body 146. The length dimension of the first extension 154 extends from the distal end of the body 146 to approximately the lengthwise midpoint of the body 146. The first extension 154 further includes a noncircular lumen 156 that extends lengthwise completely through the first extension 154. The noncircular lumen 156 has a perimeter shape that complements the perimeter shape of the stem 124 of the guide member 114, and has a size dimension that is slightly larger than the size dimension of the stem 124 such that the stem 124 may be slideably received within the lumen 156. The outer perimeter of the first extension 154 is slightly larger than the interior perimeter of the lumen 156.

The distal end of the body 146 includes a rim 158 that extends circumferentially about the distal opening 155. The rim 158 includes a superior portion 160 and an inferior portion 162. The superior portion 160 is defined by an arc existing in a plane that is normal to the longitudinal axis $A_3$ of the body 146. Thus, when viewed from the side (e.g. FIG. 21) the superior portion 160 appears to be perpendicular to axis $A_3$ of the body 146. The inferior portion 162 is defined by an arc existing in a plane that is neither normal to axis $A_3$, nor parallel to axis $A_3$. The plane of the inferior portion 162 is angled relative to the plane of the superior portion, with the angle being between 0 and 90 degrees, non-inclusive. Thus, when viewed from the side, the inferior portion 162 appears to be part of a beveled surface 164 that continues along the distal face 166 of the first extension 154. The beveled surface 164 functions to provide clearance for the facet anchor 120.

The proximal portion 150 of the superior receptacle 116 has an interruption 168 in the perimeter to limit the separation between the superior receptacle 116 and inferior receptacle 118, which consequently allows bone screws to be inserted into the superior and inferior vertebra in closer approximation adjacent the facet joint. By way of example, the interruption 168 comprises a removed section of the cylindrical body. The interruption 168 has a width dimension that is complementary to the width dimension of the second extension 188 of the inferior receptacle 118 (described below). As such, when the guide assembly 110 is assembled in use, the superior portion of the second extension 188 is snugly received within the interruption 168 so as to effectively close off the lumen 152 to tissue creep. The proximal end of the superior receptacle 116 includes a proximal opening 170, which constitutes the proximal terminus of the lumen 152.

FIGS. 22 and 23 illustrate the inferior receptacle 118 in more detail. The inferior receptacle 118 comprises a generally cylindrical body 172 having a distal portion 174, a proximal portion 176, and a lumen 178 extending longitudinally through the body 172. The distal portion 174 of the body 172 comprises an uninterrupted surface extending around the perimeter of the body 172 which functions to prevent tissue creep into the lumen 178, and a distal opening 180 that constitutes the distal terminus of the lumen 178. The distal end of the body 172 includes a rim 182 that extends circumferentially about the distal terminus of the lumen 178. The rim 182 includes an inferior portion 184 and a superior portion 186. The inferior portion 184 is defined by an arc existing in a plane that is normal to the longitudinal axis $A_4$ of the body 172. Thus, when viewed from the side (e.g. FIG. 23) the inferior portion 184 appears to be perpendicular to axis $A_4$. The superior portion 186 is defined by an arc existing in a plane that is neither normal to axis $A_4$, nor parallel to axis $A_4$. The plane of the superior portion 186 is angled relative to the plane of the inferior portion 184, with the angle being between 0 and 90 degrees, non-inclusive. Thus, when viewed from the side, the superior portion 186 appears to be a beveled surface. This beveled surface functions to provide clearance for the facet anchor 120.

The proximal portion 176 of the inferior receptacle 118 has a second extension 188 and a proximal opening 190, which constitutes the proximal terminus of the lumen 178. The second extension 188 is positioned along the superior aspect of the body 172, has a height dimension that is perpendicular the body 172 and a length dimension that is parallel to the body 172. The length dimension of the second extension 188 extends from the proximal end of the body 172 to approximately the lengthwise midpoint of the body 172. The second extension 188 further includes a noncircular lumen 192 that extends lengthwise completely through the second extension 188. The noncircular lumen 192 has a perimeter shape that complements the perimeter shape of the stem 124 of the guide member 114, and has a size dimension that is slightly larger than the size dimension of the stem 124 such that the stem 124 may be slideably received within the lumen 192. The outer perimeter of the second extension 188 is slightly larger than the interior perimeter of the lumen 192.

Figure 24:
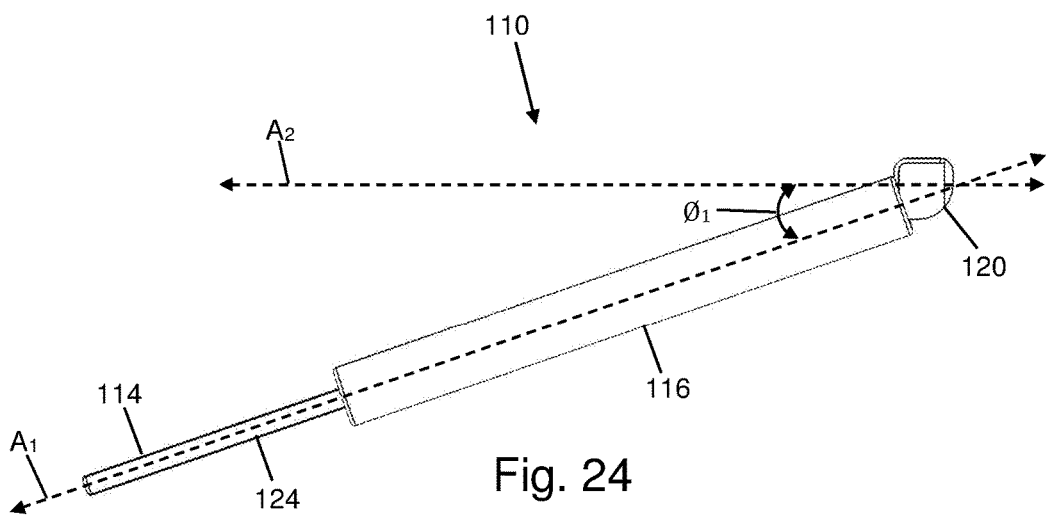
FIG. 24 is a top plan view of the guide assembly of FIG. 15.
Figure 25:
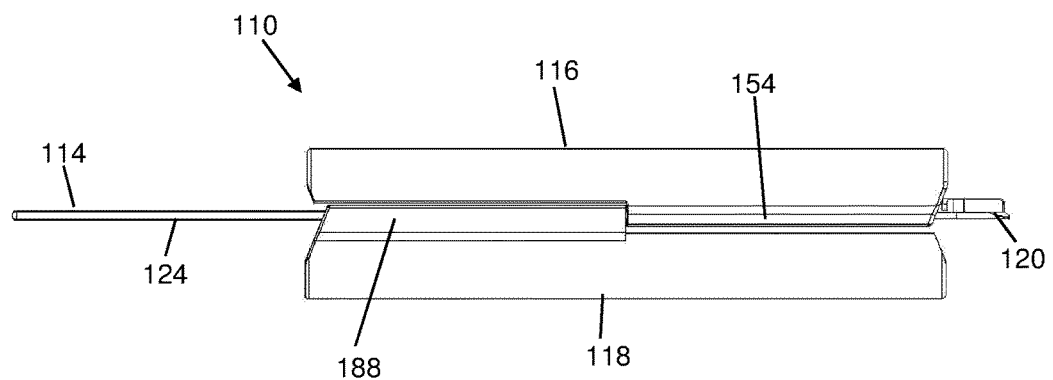
FIG. 25 is a plan view of the guide assembly of FIG. 24.

FIGS. 24 and 25 illustrate the guide assembly 110 in assembled form and without the drill guide 112. Use of the posterior cervical fusion system 400 is similar to the embodiments described previously. The first step is to insert the facet anchor 120 into the facet joint. Once the facet anchor 120 is properly seated and the appropriate insertion angle is determined, the first and second receptacles 116, 118 are selected and coupled to the guide member 114. This is accomplished by first inserting the stem 124 of the guide member 114 through the first extension 154 of the superior receptacle 116. The stem is then inserted through the second extension 188 of the inferior receptacle 118. As mentioned previously, the first and second receptacles 116, 118 are prevented from rotating about the stem 124 by way of the noncircular shape of the stem 124 and corresponding lumens in the first and second extensions 154, 188. This ensures that the angle of screw insertion (which corresponds to the offset angle Ø1 between the longitudinal axis A1 and the axis of insertion A2 of the stem 124, as discussed above) is maintained throughout the procedure.

Figure 26:
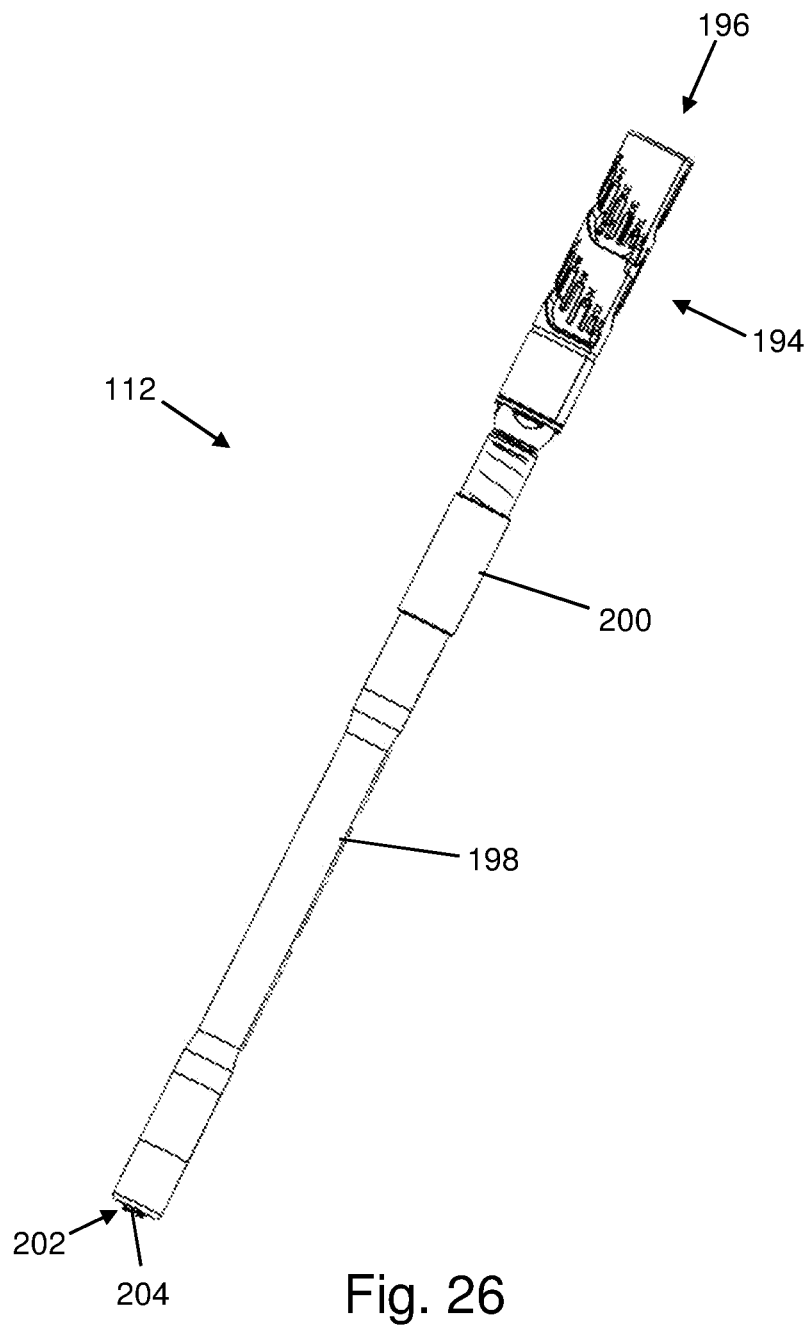
FIG. 26 is a perspective view of the drill guide forming part of the posterior cervical fusion system of FIG. 15.
Figure 27:
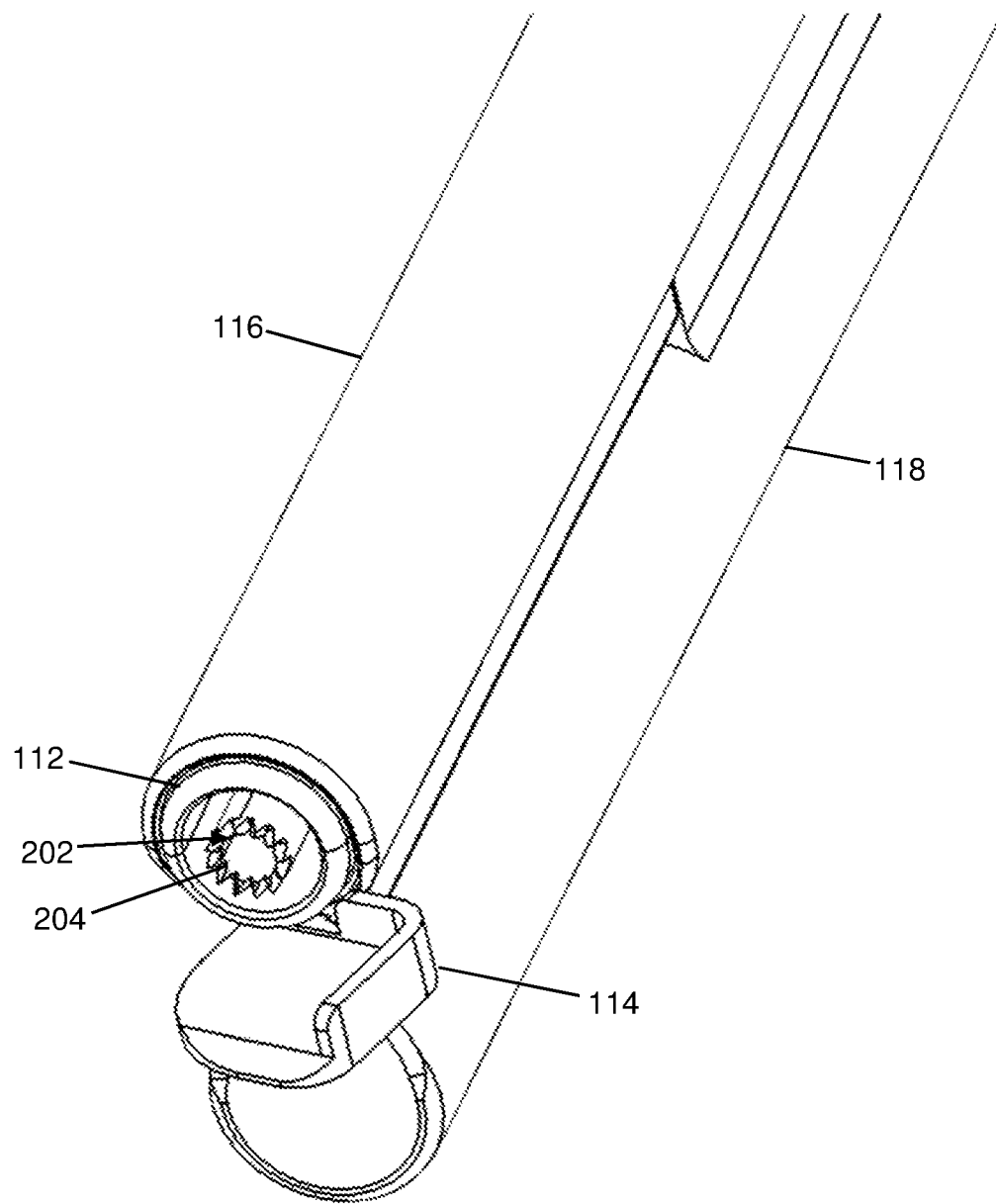
FIG. 27 is a perspective view of the distal region of the posterior cervical fusion system of FIG. 15.

The adjustable drill guide 112 will be discussed with specific reference to FIGS. 26 and 27. FIG. 26 illustrates an example of an adjustable drill guide 112 dimensioned to be received with in the superior and inferior receptacles 116, 118. FIG. 27 is a detail view of the distal end of the posterior cervical fusion system 400 fully assembled and with the drill guide 112 inserted into the superior receptacle 116. The adjustable drill guide 112 has an adjustable depth gauge 194 at the proximal end 196, allowing the surgeon to choose the desired drill depth ranging from 10 mm to 40 mm in 2 mm increments. The drill guide 112 further includes an outer housing 198 and a collar 200. The outer housing 198 is generally cylindrical and is sized and configured to be slideably received in each of the lumens 152, 178 of the first and second extensions 116, 118. Thus, the outer housing 198 has an outer perimeter dimension that is slightly smaller than the interior perimeter of the lumens 152, 178. By way of example the collar 200 is also generally cylindrical in shape and is positioned at the proximal end of the outer housing 198. The collar 200 has a perimeter that is greater than the perimeter of the proximal openings 170, 190 of the superior and inferior receptacles 116, 118, so as to act as a depth stop when inserting the drill guide 112 into the receptacle. The distal tip 202 of the drill guide 112 has serrations 204 or other suitable anti-migration features to stabilize the position of the drill guide 112 and receptacle during drilling.

Any other conventional surgical instrumentation may be used in conjunction with the various embodiments of the present invention. This includes instruments to decorticate the bone, bone probes and reduction and compression devices.

The various embodiments of the present invention provide a posterior cervical screw system that can be readily and securely installed in a variety of surgical situations, including during open surgery, using minimally invasive techniques, using a percutaneous approach or using a tubular or expandable minimally invasive retractor. The device creates structural support for the cervical spine and allows fusion of the cervical area.

The above descriptions are those of current embodiments of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles "a," "an," "the" or "said," is not to be construed as limiting the element to the singular.

What is claimed is:

1. A method of performing posterior cervical fixation surgery, comprising:
    establishing an operative window to expose a cervical facet joint of a patient, including a superior facet and an inferior facet of adjacent vertebrae;
    introducing a guide member into the operative window, the guide member including a facet sled and a handle, the facet sled comprising a thin block adapted for insertion into a vertebral facet joint between a superior facet and inferior facet of a patient, the thin block having a top surface, a bottom surface, a leading end, a trailing end, a lateral side, and a medial side, wherein the handle is adapted to slideably receive a first extension and a second extension such that the angular position of the first extension and second extension about a longitudinal axis of the handle are maintained;
    positioning the facet sled within the facet joint such that the handle extends at a desired angle in a medial direction;
    slideably coupling the first extension to the handle such that the distal end of the first extension is adjacent the superior facet, the first extension having a generally tubular shape and an interior lumen adapted to receive a surgical instrument therethough, the first extension further having a first handle receiver sized and configured to slideably interconnect with the handle;
    slideably coupling the second extension to the handle such that the distal end of the second extension is adjacent the inferior facet, the second extension having a generally tubular shape and an interior lumen adapted to receive a surgical instrument therethough, the second extension further having a second handle receiver sized and configured to slideably interconnect with the handle; and
    advancing a surgical instrument through the lumen of the first extension to perform at least a portion of a surgical procedure.

2. The method of claim 1, further comprising the step of advancing a surgical instrument through the lumen of the second extension to perform at least a portion of the surgical procedure.

3. The method of claim 1, further comprising sequentially uncoupling the first and second extensions from the guide member.

4. The method of claim 3, further comprising removing the facet sled from the facet joint.

5. The method of claim 1, wherein the thin block of the facet sled includes a raised back wall on the top surface that extends along at least a portion of the trailing end.

6. The method of claim 5, wherein the step of positioning the facet sled within the facet joint includes advancing the thin block into the facet joint until the raised back wall abuts the facet.

7. The method of claim 1, wherein the thin block of the facet sled includes a raised lateral wall on the top surface that extends along at least a portion of the lateral side.

8. The method of claim 7, wherein the step of positioning the facet sled within the facet joint includes advancing the thin block into the facet joint until the raised lateral wall abuts the facet.

9. The method of claim 1, wherein the thin block of the facet sled includes a raised back wall on the top surface that extends along at least a portion of the trailing wall and a raised lateral wall on the top surface that extends along at least a portion of the lateral side.

10. The method of claim 7, wherein the step of positioning the facet sled within the facet joint includes advancing the thin block into the facet joint until each of the raised back wall and raised lateral wall abuts the facet.

11. The method of claim 1, wherein the leading end meets the lateral side at a first corner and meets the medial side at a second corner, the trailing end meets the lateral side at a third corner and the medial side at a fourth corner.

12. The method of claim 11, wherein the second corner has a larger radius of curvature than any of the first, second and third corners.

13. The method of claim 1, wherein the handle has a non-circular perimeter.

14. The method of claim 13, wherein the perimeter of the handle is generally rectangular.

15. The method of claim 1, wherein the first handle receiver extends along a side of the first extension from a distal end of the first extension to a midpoint along the length of the first extension.

16. The method of claim 15, wherein the second handle receiver extends along a side of the first extension from a proximal end of the second extension to a midpoint along the length of the second extension.

17. The method of claim 1, wherein the distal end of the first extension includes a first rim that extends circumferentially about a first distal opening, the first rim having a first superior portion and a first inferior portion, the first superior portion being defined by an arc existing in a plane that is normal to a third longitudinal axis of the first extension.

18. The method of claim 17, wherein the first inferior portion is defined by an arc existing in a plane that is neither normal to the third longitudinal axis or parallel to the third longitudinal axis.

19. The method of claim 1, wherein the distal end of the second extension includes a second rim that extends circumferentially about a second distal opening of the second extension, the second rim having a second superior portion and s second inferior portion, the second inferior portion being defined by an arc existing in a plane that is normal to a fourth longitudinal axis of the second extension.

20. The method of claim 19, wherein the second superior portion is defined by an arc existing in a plane that is neither normal to the fourth longitudinal axis or parallel to the fourth longitudinal axis.

\* \* \* \* \*